(12) United States Patent
Fukuda

(10) Patent No.: US 6,646,255 B2
(45) Date of Patent: Nov. 11, 2003

(54) LIQUID CHROMATOGRAPH/MASS SPECTROMETER AND ITS IONIZATION INTERFACE

(75) Inventor: Mitsuaki Fukuda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/013,723

(22) Filed: Dec. 13, 2001

(65) Prior Publication Data

US 2002/0074491 A1 Jun. 20, 2002

(30) Foreign Application Priority Data

Dec. 15, 2000 (JP) .................................... 2000-381590

(51) Int. Cl.[7] ............................................... H01J 49/00
(52) U.S. Cl. ........................ 250/288; 250/281; 250/294
(58) Field of Search .................... 250/281, 282–300, 250/427, 423 R; 436/173

(56) References Cited

U.S. PATENT DOCUMENTS 4,888,482 A * 12/1989 Kato ........................... 250/288
5,726,447 A * 3/1998 Aisawa et al. ............... 250/288
6,207,954 B1 * 3/2001 Andrien et al. .............. 250/288

* cited by examiner

Primary Examiner—John R. Lee
Assistant Examiner—James P. Hughes
(74) Attorney, Agent, or Firm—Armstrong, Westerman & Hattori, LLP

(57) ABSTRACT

The present invention proposes a liquid chromatograph/mass spectrometer constructed to present a maximized or almost maximized ion-producing efficiency of APCI, irrespective of whether positive or negative ions are produced. In an embodiment of the invention, two discharging electrodes 222, 223 for ionizing solvent gas molecules are disposed ahead of a sprayer 221 for spraying sample droplets; one electrode is disposed at the position optimal to the positive ion production, and another electrode is disposed at the position optimal to the negative ion production. In the analyzing operation, the same high voltage is applied to the discharging electrodes 222, 223 to generate corona discharge. According to whether positive or negative ions are to be produced, one of the discharging electrodes dominantly contributes to the ionization. Thus, the ion-producing efficiency is almost maximized irrespective of whether positive or negative ions are produced.

12 Claims, 3 Drawing Sheets

LIQUID CHROMATOGRAPH/MASS SPECTROMETER AND ITS IONIZATION INTERFACE

The present invention relates to a liquid chromatograph/ mass spectrometer (LC/MS), and particularly to an atmospheric pressure ionization interface of an LC/MS disposed between the liquid chromatograph (LC) part and the mass spectrometer (MS) part.

BACKGROUND OF THE INVENTION

In an LC/MS, a sample liquid is separated into components by the column in the LC part, and the components, flowing out of the column at different time points, are ionized by an ionization interface and introduced into the MS part. The ionization interface includes an ionizer first to change the sample liquid to mist by means of heat, high-velocity gas flow, high voltage electric field, etc, and then to produce gaseous ions from the mist. Some widely used ionizers utilize the so-called atmospheric ionization method, such as atmospheric pressure chemical ionization (APCI) or electrospray ionization (ESI). In an APCI, for example, a nozzle connected to the outlet of the column in the LC part is disposed with its exit port directed to the inside of the ionization chamber which is maintained substantially at the atmospheric pressure, and a needle-like discharging electrode is disposed ahead of the exit port of the nozzle. The sample liquid is heated into mist at the nozzle, and the droplets of the mist are brought into reaction with the solvent ions (or buffer ions) produced by corona discharge from the discharging electrode. Thus, the sample ions are produced. In an ESI, on the other hand, a high voltage of about several kilovolts is applied to the tip of the nozzle to produce a strong non-uniform electric field there. Due to the non-uniform electric field, electric charges in the sample liquid are separated, and the Coulomb force breaks the sample liquid into mist or droplets. The solvent contained in the droplets evaporates when they contact the ambient air. Thus, the gaseous ions are produced.

With the above-described ionizer, either a positive ionization, where electrons are stripped from the sample molecules, or a negative ionization, where electrons are donated to the sample molecules, is selected depending principally on the kinds of the sample components. In the case of APCI, the optimal position of the discharging electrode to maximize the ion-producing efficiency in the positive ionization is not always the same as that in the negative ionization. Therefore, in the conventional APCI type ionizer, if either positive or negative ions are to be produced, the discharging electrode is adjusted to the position where the ion-producing efficiency is maximized for the selected ionization method. A sample, however, is often a mixture of different components: some tend to become positive ions and others tend to become negative ions. When this type of sample is to be analyzed, a design which compromises the maximum efficiency in both cases has hithertofore inevitably been chosen such that the discharging electrode is disposed at an intermediate place where the ion-producing efficiency is not optimal either for the positive or negative ionization. This design decreases the number of ions introduced into the MS part, and deteriorates the accuracy and sensitivity of the analysis.

In order to solve the above problems, the present invention proposes an LC/MS constructed to present a maximized or almost maximized ion-producing efficiency of APCI, irrespective of whether the positive or negative ions are produced.

SUMMARY OF THE INVENTION

Thus, a liquid chromatograph/mass spectrometer (LC/MS) according to the present invention includes a liquid chromatograph part for separating a sample liquid into components according to their retention times, an ionizer for changing the components to ions by an atmospheric pressure chemical ionization method, and an interface for introducing the ions into a mass spectrometer part, wherein:

the ionizer includes a sprayer and a plurality of discharging electrodes disposed ahead of the sprayer, where the sprayer sprays the separated components of the sample liquid into a space at a substantially atmospheric pressure and the plurality of electrodes ionize molecules of a mobile phase solvent; and one discharging electrode is disposed at a position optimal to a positive ion production, and another discharging electrode is disposed at a position optimal to a negative ion production.

FIG. 5 roughly shows the relationship between the ion-producing efficiency and the distance between the tip of the discharging electrode and the central axis C of the sprayer. FIG. 5 teaches that the optimal position of the discharging electrode for the positive ion production is closer to the central axis C than that for the negative ion production. Thus, in the LC/MS according to the present invention, one (or the first) discharging electrode is disposed at the position optimal to the positive ion production, and another (or the second) discharging electrode is disposed at the position optimal to the negative ion production, and a positive or negative high voltage is equally applied to all the electrodes according to whether positive or negative ions are to be produced. The application of the voltage generates corona discharge from both the first and second discharging electrodes, where the ions produced from the mobile phase solvent molecules by the corona discharge generated from one of the two discharging electrodes dominantly contribute to the ionization of the sample molecules, depending on whether positive or negative ions are produced.

Thus, with the LC/MS according to the present invention, the ion-producing efficiency is maintained at an almost maximized level irrespective of whether positive or negative ions are produced. As a result, a greater number of ions are introduced into the MS part, enhancing the accuracy and sensitivity of the analysis. Also, the present invention omits the conventional time-consuming work of adjusting the exact position of the discharging electrode, depending on whether positive or negative ions are to be produced. Thus, the analysis work can be carried out efficiently.

DETAILED DESCRIPTION OF A PREFERRED EMBODIMENT

Figure 1:
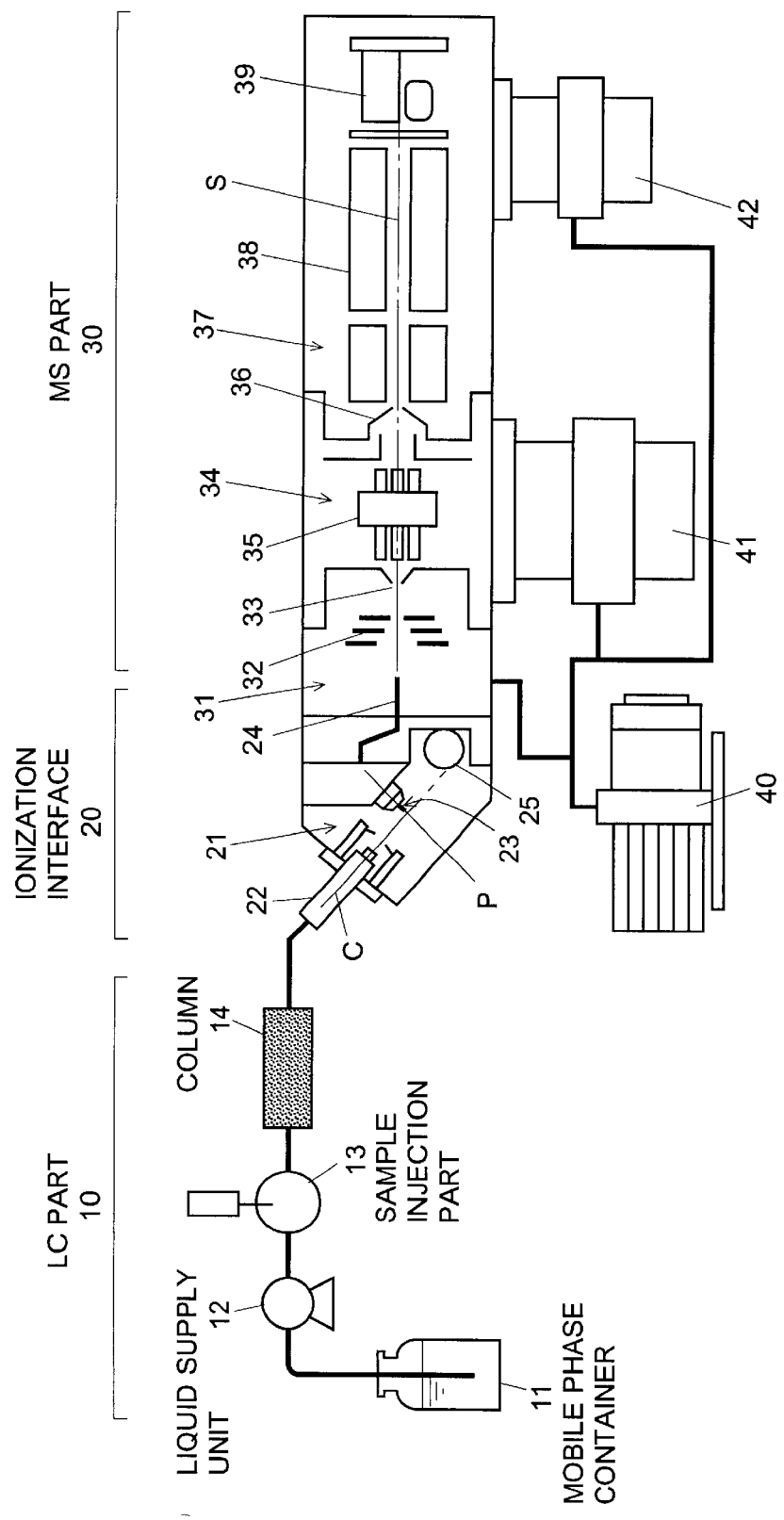
FIG. 1 schematically shows the main part of an LC/MS embodying the present invention.

An LC/MS embodying the present invention is described referring to the drawings. FIG. 1 shows the construction of the LC/MS of the present embodiment, having an LC part 10, ionization interface 20 and MS part 30.

In the LC part 10, a liquid supply unit 12 draws the mobile phase from a mobile phase container 11 and supplies it to a sample injection part 13 at a fixed flow rate. In the sample injection part 13, the sample liquid is injected into the mobile phase with a predetermined timing. The mobile phase with the sample liquid mixed therein is sent to a column 14 and separated into components while passing through the column 14. The components flow out of the column 14 at different time points depending on the different retention times.

The ionization interface 20 includes an ionization chamber 21, in which an ionization probe 22 connected to the outlet of the column 14 is disposed. In the MS part 30, the space between a mass spectrometric chamber 37 and the ionization chamber 21 is partitioned into a first intermediate chamber 31 and a second intermediate chamber 34. The mass spectrometric chamber 37 includes a quadrupole filter 38 and an ion detector 39; the first intermediate chamber 31 and the second intermediate chambers 34 include a first ion lens 32 and a second ion lens 35, respectively. The ionization chamber 21 and the first intermediate chamber 31 communicate with each other only through a desolvation tube 24 of a small inner diameter, and the first intermediate chamber 31 and the second intermediate chamber 34 communicate with each other only through a skimmer 33 having a hole with a small diameter.

The ionization chamber 21 is continuously supplied with the gasified molecules of the sample liquid from the ionization probe 22, thus being maintained approximately at the atmospheric pressure. The mass spectrometric chamber 37, on the other hand, is evacuated with a turbo molecular pump (TMP) 42 to a high vacuum of about $10^{-3}$ to $10^{-4}$ Pa. In order to provide a passage for ions to travel from the ionization chamber 21 to the mass spectrometric chamber 37 despite that the great pressure difference between the two chambers, the first and second intermediate chambers 31 and 34 are disposed between the above two chambers to gradually decrease the pressure. For example, the first intermediate chamber 31 is evacuated with a rotary pump (RP) 40 to about $10^2$ Pa, and the second intermediate chamber 34 is evacuated with a turbo molecular pump (TMP) 41 to about $10^{-1}$ to $10^{-2}$ Pa.

The sample liquid is sprayed from the tip of the ionization probe 22 into the ionization chamber 21, where the sample molecules are ionized by chemical reaction with the mobile phase solvent ions, as will be described later. Thus generated ions, together with the droplets that are not ionized, are drawn into the desolvation tube 24 due to the pressure difference between the ionization chamber 21 and the first intermediate chamber 31. The first ion lens 32 generates an electric field to assist the introduction of the ions through the desolvation tube 24 and to converge the ions at or in the proximity of the hole of the skimmer 33. The ions introduced into the second intermediate chamber 34 through the hole of the skimmer 33 are converged and accelerated by the second ion lens 35, and are sent to the mass spectrometric chamber 37 through a small hole 36. In the mass spectrometric chamber 37, only such ions that have a particular mass number (m/z: where m is mass and z is charge) pass through the space within the quadrupole filter 38 along the longitudinal axis, and reach the ion detector 39, where a corresponding electric current is generated.

Referring to FIG. 1, the central axis P of the entrance 23 of the desolvation tube 24 is obliquely directed at about 45° to the ion beam axis S of the subsequent part. The ionization probe 22 for spraying the sample liquid is attached to the chamber with its central axis C directed so that the sample liquid is sprayed in the direction approximately perpendicular to the central axis P of the entrance 23. A drain 25 for collecting the sprayed liquid sample is disposed ahead of the ionization probe 22 in the spraying direction. Most of the droplets of the sample and sample ions generated after the spraying enter the desolvation tube 24 from the entrance 23, while the rest of the droplets are collected by the drain 25 and flow out.

Figure 2:
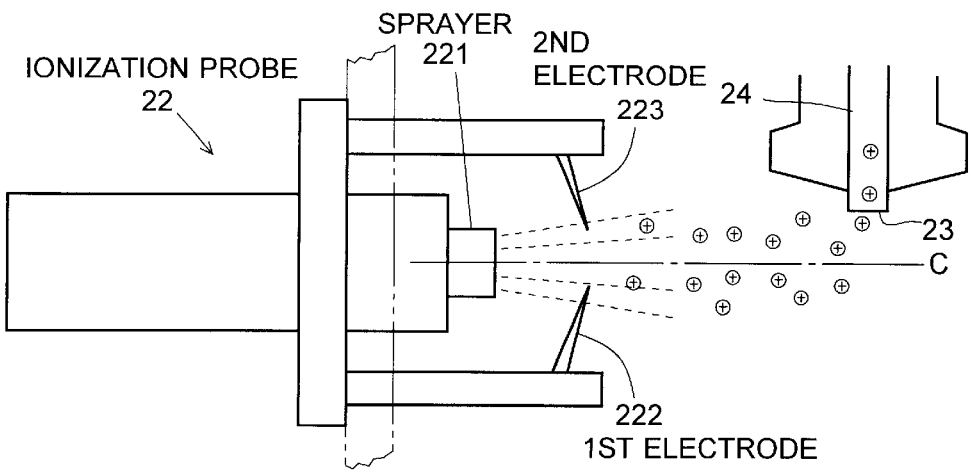
FIG. 2 shows the detailed structure of the part including the ionization probe in FIG. 1.
Figure 3:
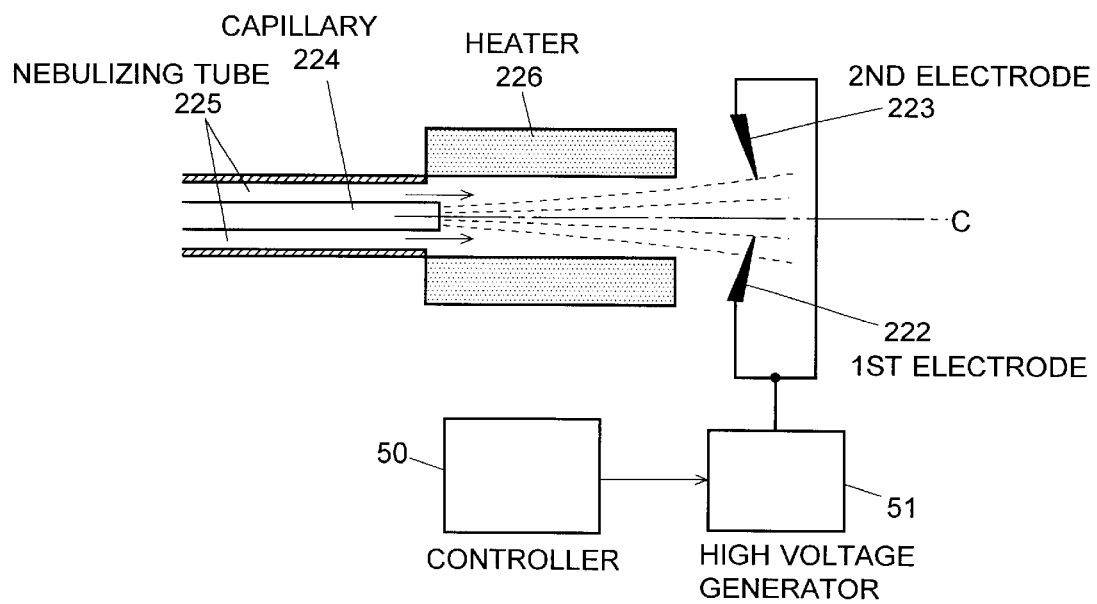
FIG. 3 shows the schematic structure of the inside of the ionization probe and the electrical construction of the main part of the same.

Detailed structure of the ionization probe 22 is described referring to FIGS. 2 and 3. As shown in FIG. 2, the ionization probe 22 includes a sprayer 221 and two pieces of needle-shaped discharging electrodes 222, 223 (first discharging electrode 222 and second discharging electrode 223) disposed ahead of the sprayer 221. The sprayer 221, as shown in FIG. 3, includes a capillary 224 for passing the sample liquid and a nebulizing tube 225 coaxially surrounding the capillary 224. On reaching the end of the capillary 224, the sample liquid is broken into droplets and spouted into the chamber 21 with the aid of the nebulizing gas (normally $N_2$ gas) blowing from the nebulizing tube 225. The space ahead of the capillary 224 is surrounded by a heater 226, and the solvent contained in the droplets is vaporized into a solvent gas by the heat from the heater 226. When a high voltage is applied from a high voltage generator 51 to the discharging electrodes 222, 223, corona discharge occurs in the space, whereby the solvent gas molecules change to solvent ions. The solvent ions chemically react with the sample molecules in the droplets, whereby the sample molecules are ionized into sample ions.

Figure 4:
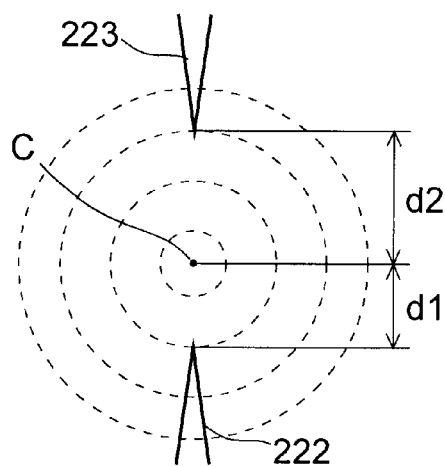
FIG. 4 shows the discharging electrodes viewed from the right side in FIG. 3.
Figure 5:
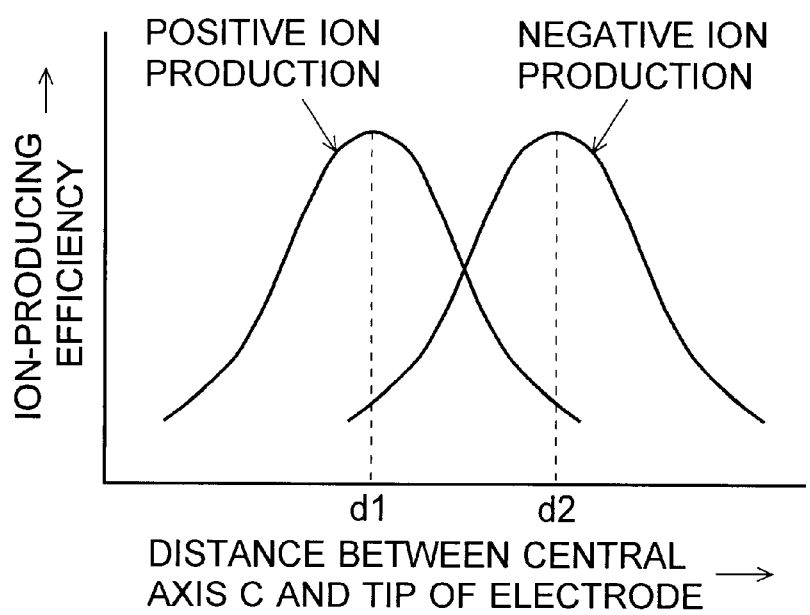
FIG. 5 is a graph showing the relation between the ion-producing efficiency and the radial distance between the tip of the discharging electrode and the central axis C of the ionization probe (or axis of spray).

A method of determining the optimal positions of the discharging electrodes 222 and 223 is described referring to FIGS. 4 and 5. As shown in FIG. 5, the optimal position of the discharging electrode for the positive ion production is closer to the central axis C than that for the negative ion production. Therefore, as shown in FIG. 4, the first discharging electrode 222 is adjusted to the position where the positive ions are produced most efficiently (at distance d1 from the central axis C), and the second discharging electrode 223 is adjusted to the position where the negative ions are produced most efficiently (at distance d2).

In an analyzing operation, the controller 50 controls the high voltage generator 51 to generate either positive or negative high voltage according to whether positive or negative ions are to be produced. Accordingly, the same high voltage is applied to both discharging electrodes 222, 223, and corona discharge occurs from both discharging electrodes 222, 223. The solvent gas molecules are ionized by the corona discharge from either of the electrodes, where, however, the corona discharge generating from one electrode contributes to the production of ions far more greatly than that from the other electrode. The electrode that makes a greater contribution to the ion production depends on whether positive or negative ions are produced. In any case, ions are produced at high efficiency.

In the above embodiment, the positions of the discharging electrodes 222, 223 are adjusted only in its radial distance from the central axis C. It is also possible to adjust the positions along the central axis C. However, since it is the radial distance from the central axis C that greatly influences the ion-producing efficiency, an adequate effect can be obtained even by a sole adjustment of the radial distance. It is further possible to use more than two discharge electrodes.

It should be noted that above embodiment is a mere example, which can be further changed or modified within the spirit and scope of the present invention.

What is claimed is:

1. A liquid chromatograph/mass spectrometer including a liquid chromatograph part for separating a sample liquid into components according to their retention times, an ionizer for changing the components to ions by an atmospheric pressure chemical ionization method, and an interface for introducing the ions into a mass spectrometer part, wherein:

the ionizer includes a sprayer and a plurality of discharging electrodes disposed ahead of the sprayer, where the sprayer sprays the separated components of the sample liquid into a space at a substantially atmospheric pressure and the plurality of electrodes ionize molecules of a mobile phase solvent; and one discharging electrode is disposed at a position optimal to a positive ion production, and another discharging electrode is disposed at a position optimal to a negative ion production.

2. The liquid chromatograph/mass spectrometer according to claim 1, wherein radial distances between a central axis of spraying the separated components and the tips of said one and another discharging electrodes are determined so that the tip of said one discharging electrode is adjusted to a distance optimal to the positive ion production, and the tip of said another discharging electrode is adjusted to a distance optimal to the negative ion production.

3. The liquid chromatograph/mass spectrometer according to claim 2, wherein the positions in the direction of spraying the separated components of said one and another discharging electrodes are determined so that said one discharging electrode is adjusted to a position optimal to the positive ion production, and said another discharging electrode is adjusted to a position optimal to the negative ion production.

4. The liquid chromatograph/mass spectrometer according to claim 1, which comprises more than two discharging electrodes.

5. The liquid chromatograph/mass spectrometer according to claim 2, which comprises more than two discharging electrodes.

6. The liquid chromatograph/mass spectrometer according to claim 3, which comprises more than two discharging electrodes.

7. An ionization interface for a liquid chromatograph/mass spectrometer having a liquid chromatograph part for separating a sample liquid into components according to their retention times, said interface including an ionizer for changing the components to ions by an atmospheric pressure chemical ionization method and means for introducing the ions into a mass spectrometer part, wherein:

the ionizer includes a sprayer and a plurality of discharging electrodes disposed ahead of the sprayer, where the sprayer sprays the separated components of the sample liquid into a space at a substantially atmospheric pressure and the plurality of electrodes ionize molecules of a mobile phase solvent; and one discharging electrode is disposed at a position optimal to a positive ion production, and another discharging electrode is disposed at a position optimal to a negative ion production.

8. The ionization interface according to claim 7, wherein radial distances between a central axis of spraying the separated components and the tips of said one and another discharging electrodes are determined so that the tip of said one discharging electrode is adjusted to a distance optimal to the positive ion production, and the tip of the second discharging electrode is adjusted to a distance optimal to the negative ion production.

9. The ionization interface according to claim 8, wherein the positions in the direction of spraying the separated components of said one and another discharging electrodes are determined so that said one discharging electrode is adjusted to a position optimal to the positive ion production, and said another discharging electrode is adjusted to a position optimal to the negative ion production.

10. The ionization interface according to claim 7, which comprises more than two discharging electrodes.

11. The ionization interface according to claim 8, which comprises more than two discharging electrodes.

12. The ionization interface according to claim 9, which comprises more than two discharging electrodes.

* * * * *